United States Patent [19]

Mann

[11] Patent Number: 5,462,517
[45] Date of Patent: * Oct. 31, 1995

[54] KNEE BRACE HAVING AN INFLATABLE BLADDER SUPPORT

[75] Inventor: Donaerl B. Mann, High Springs, Fla.

[73] Assignee: D'Mannco, Inc., High Springs, Fla.

[*] Notice: The portion of the term of this patent subsequent to Jan. 31, 2012, has been disclaimed.

[21] Appl. No.: 294,086

[22] Filed: Aug. 22, 1994

Related U.S. Application Data

[63] Continuation-in-part of Ser. No. 904,844, Jun. 26, 1992, Pat. No. 5,385,538.

[51] Int. Cl.⁶ ............................................. A61F 5/04
[52] U.S. Cl. ................................. 602/26; 602/5; 602/13
[58] Field of Search .................................. 602/5, 13, 26, 602/23, 62; 128/DIG. 20

[56] References Cited

U.S. PATENT DOCUMENTS 3,548,820 12/1970 Bergen .
4,353,362 10/1982 DeMarco .
4,379,463 4/1983 Meier et al. .
4,872,448 10/1989 Johnson, Jr. .
5,385,538 1/1995 Mann ........................................ 602/26

*Primary Examiner*—Richard J. Apley
*Assistant Examiner*—Beverly M. Flanagan
*Attorney, Agent, or Firm*—James E. Larson; Herbert W. Larson

[57] ABSTRACT

A cloth body having a central knee hole wrapped around a patient's knee to treat knee flexion contractures. Hook and loop straps secure the cloth body to the patient's knee. Longitudinally extending pockets on opposite sides of the knee hole contain a longitudinal support element and an air bladder. Inflation of the air bladder supports the patient's knee in a rigid position. Latitudinally extending pockets surrounding the posterior portion of the thigh and calf contain a flexible support element.

17 Claims, 9 Drawing Sheets

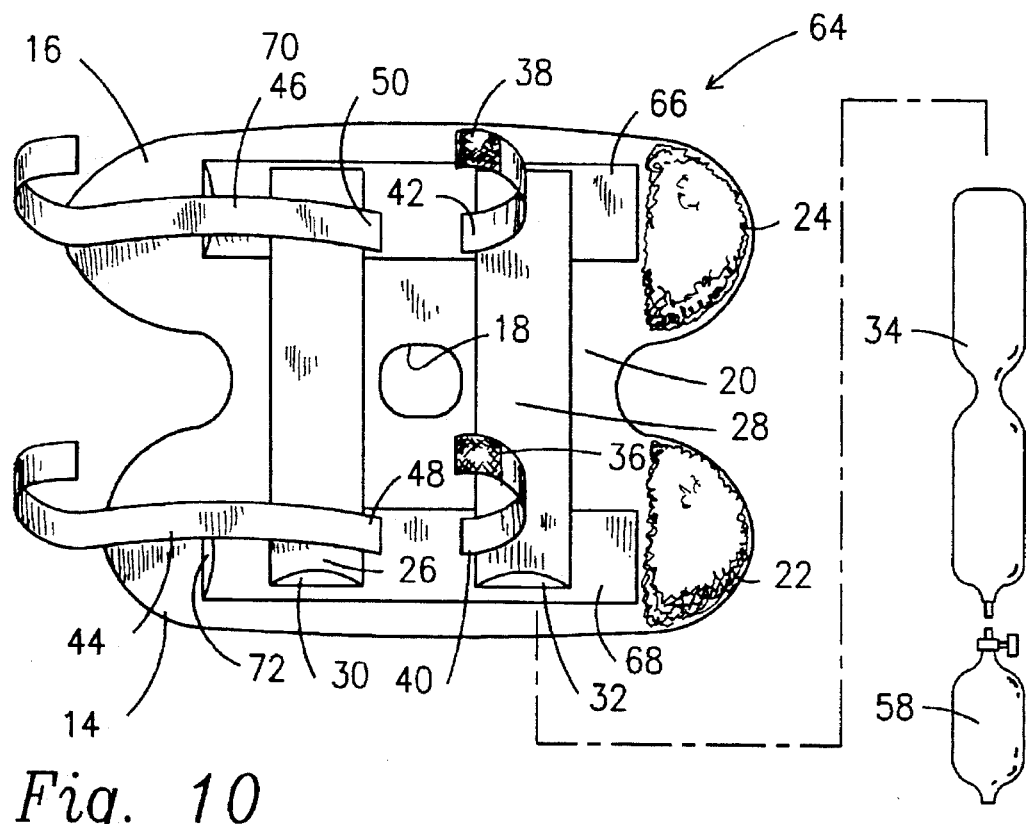
Fig. 10
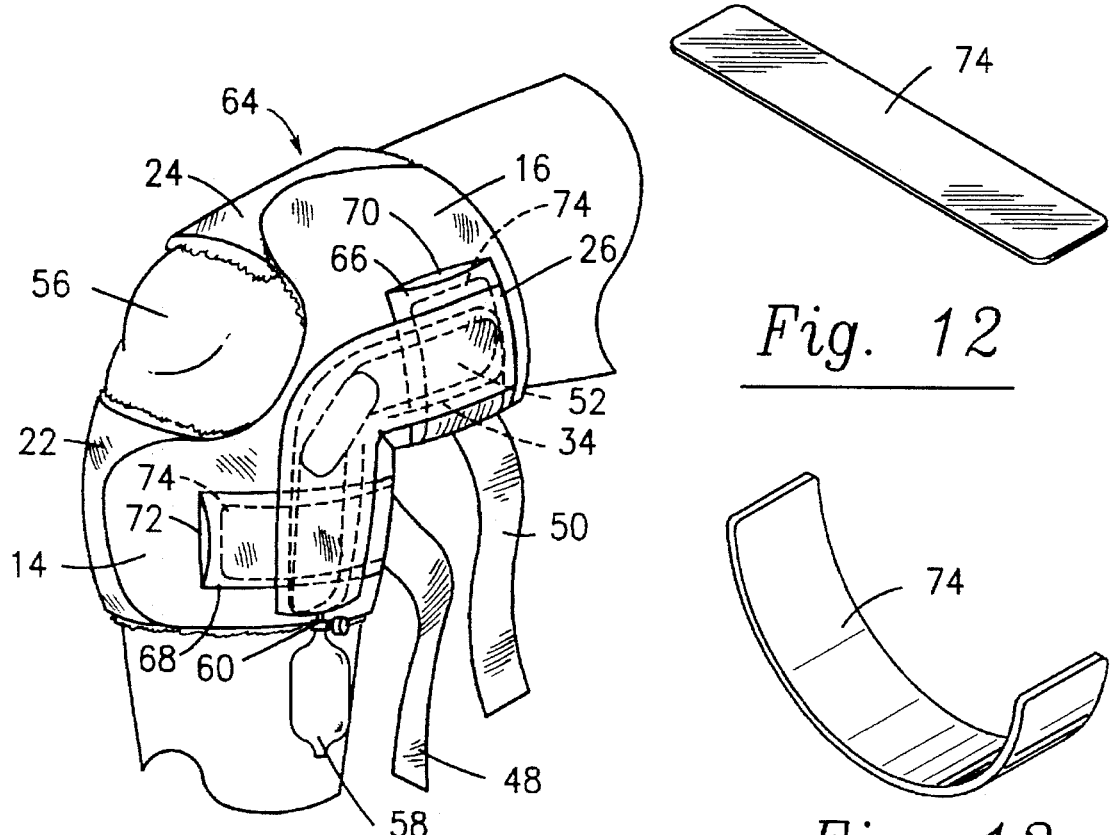
Fig. 11
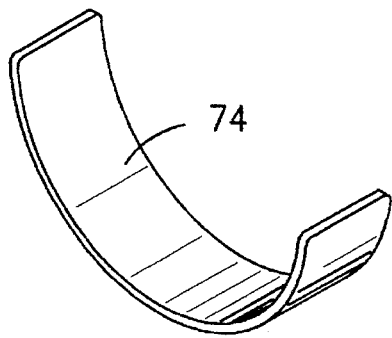
Fig. 12
Fig. 13

KNEE BRACE HAVING AN INFLATABLE BLADDER SUPPORT

This application is a continuation-in-part of application Ser. No. 07/904,844, filed on Jun. 26, 1992 now U.S. Pat. No. 5,385,538.

BACKGROUND OF THE INVENTION

1. Field of the Invention

This invention relates to orthopedic knee brace appliances. More particularly it refers to an orthopedic appliance applied to a patient's knee, the appliance containing an air bladder inflated to retain the knee in a rigid configuration.

2. Description of Prior Art

Many orthopedic appliances exist containing air bladders or fluid control chambers for intermittently supporting and releasing support on body parts. U.S. Pat. No. 3,993,056 describes such appliances having inflatable tubes stitched into a fabric extending vertically over a portion of the fabric. U.S. Pat. No. 4,430,042 describes a pillow type device strapped to a leg and then inflated. U.S. Pat. No. 4,872,448 describes a U-shaped inflatable air bladder over the patella. U.S. Pat. No. 4,938,207 describes a linear brace employing first and second fluid filled chambers. U.S. Pat. No. 4,947,834 describes a brace for compressing a patient's outer extremities, the brace having flexible chambers arranged one after another in a series and these are successively inflated. U.S. Pat. No. 4,960,115 describes a body support apparatus having at least two inflation chambers.

None of these appliances provides a means to alternately support a patient's knee in various positions and permit easy removal and reapplication of the splint for treating wounds under the brace. A need exists to have flexibility in a knee brace support appliance for treating knee flexion contractures and to obtain ease of removing and reapplying the brace.

SUMMARY OF THE INVENTION

I have invented a knee brace having an inflatable bladder support to treat knee flexion contractures. My knee brace has a cloth body having a soft bottom portion in contact with the patient's skin and a fabric top surface to which longitudinal pockets are attached, each longitudinal pocket containing a plastic air bladder and either a rigid support or a hinged support element. In a preferred embodiment, latitudinal pockets are additionally attached to the top surface, each latitudinal pocket containing a flexible support element to position along the posterior portion of the thigh and calf. Hook and loop straps are attached to the top surface and an area from which a patella portion of the knee can protrude is provided. A hand pump is attached to the bladder to inflate or deflate the bladder as needed by the patient. The wrap around fastening of the cloth body allows for treatment of wounds and incisions by unfastening the hook and loop closures, treating the wound, and easily reapplying the brace. Straps having hook and loop material are attached to the top surface of the cloth body providing a means to securely employ the appliance around the knee of a patient.

In an alternate embodiment, an exoskeleton frame is provided in place of the hinged or rigid support elements and flexible support elements for surrounding the cloth body and providing a means to set the knee in a multiplicity of fixed positions. The exoskeleton frame is secured to the cloth body by straps having hook and loop material surrounding the outer surface of the cloth body.

BRIEF DESCRIPTION OF THE DRAWINGS

The invention may be best understood by those having ordinary skill in the art by reference to the following detailed description when considered in conjunction with the accompanying drawings in which:

FIG. 10 is a top plan view of a preferred embodiment of the orthopedic appliance of my invention prior to applying the preferred appliance to a patient.

FIG. 11 is a perspective view of the preferred orthopedic appliance positioned on a patient's knee with an air bladder, polycentric support element, and a pair of flexible support elements shown in phantom.

FIG. 12 is a perspective view of a flexible support element used in the preferred orthopedic appliance prior to being molded to the shape of the posterior portion of a thigh or calf of a patient's leg.

FIG. 13 is a perspective view of the flexible support element used in the preferred orthopedic appliance after being molded to the shape of the posterior portion of the thigh or calf of a patient's leg.

DETAILED DESCRIPTION OF THE INVENTION

Figure 1:
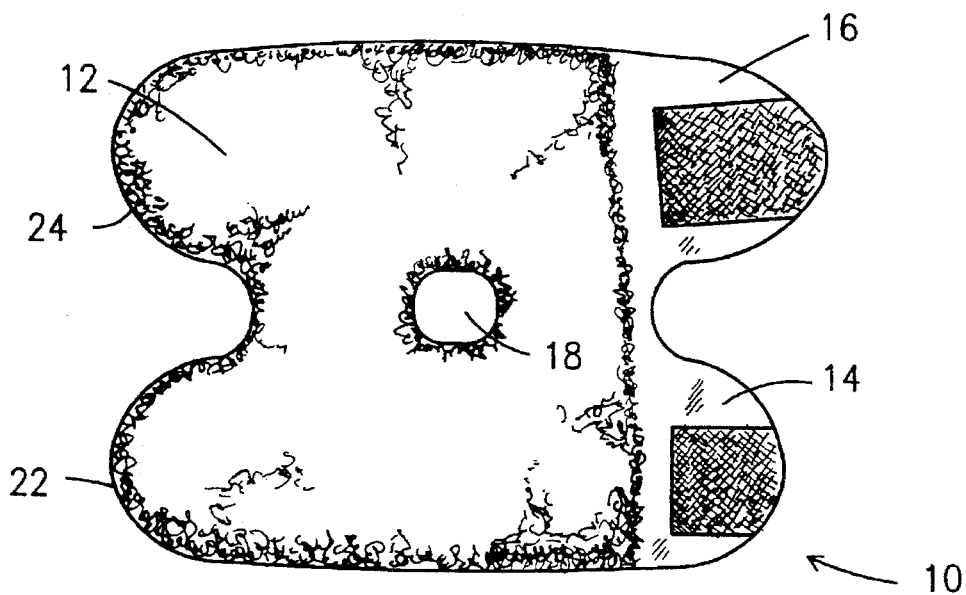
FIG. 1 is a bottom plan view of the orthopedic appliance of my invention prior to applying the appliance to a patient.

Throughout the following detailed description, the same reference numerals refer to the same elements in all figures.

The knee brace 10 is shown in FIG. 1 presenting a bottom plan view thereof. The bottom portion is covered by a pile 12 such as KODEL, a registered trademark for a product sold by Eastman Kodak Company, or other soft wool or wool like material which will not be abrasive to a patient's skin surface. A short section 14 and a longer section 16 projecting from the pile 12 of hook and loop material are used in fastening the brace 10 to a patient's knee A hole 18 approximately centrally located in the pile material 12 exposes a posterior portion of the knee.

Figure 2:
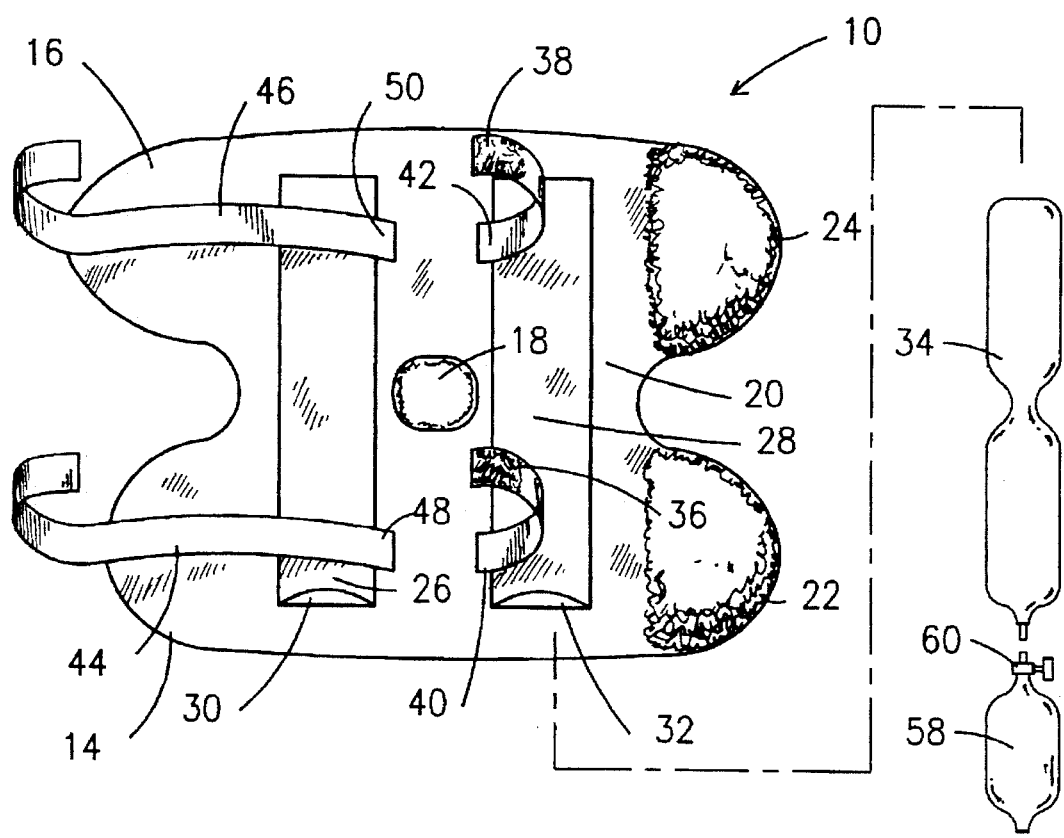
FIG. 2 is a top plan view of the orthopedic appliance shown in FIG. 1.
Figures 3, 4, 5, 6:
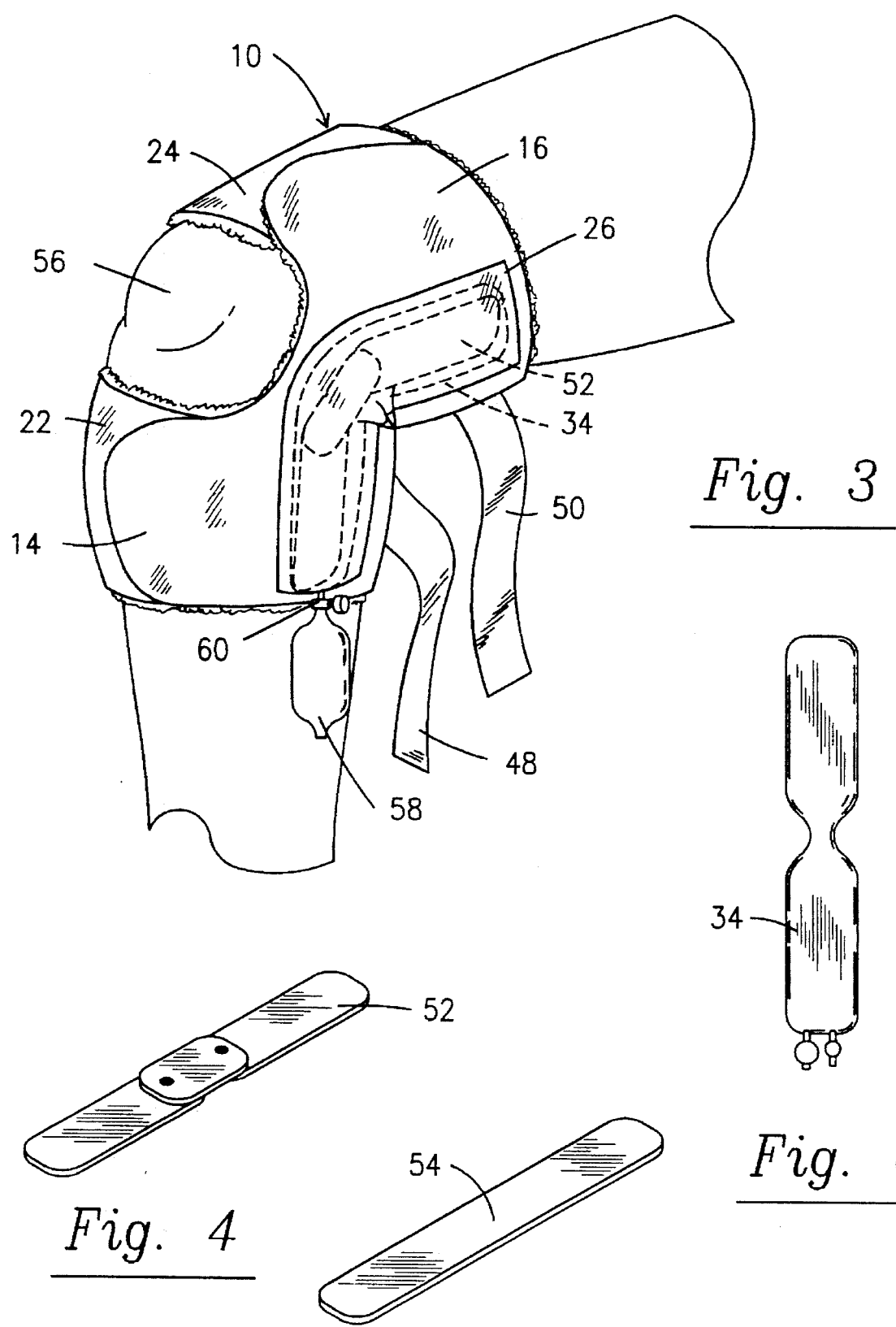
FIG. 3 is a perspective view of the orthopedic appliance shown in FIG. 1, positioned on a patient's knee with an air bladder and polycentric support element shown in phantom.
FIG. 4 is a perspective view of the polycentric support element.
FIG. 5 is a perspective view of a rigid support element.
FIG. 6 is a top plan view of the air bladder which inserts within a pocket.

FIG. 2 shows a top plan view of the knee brace 10. The top surface of the brace is covered by tightly woven fabric 20. A pair of projecting sections 22 and 24, oppositely positioned sections 14 and 16 respectively, have hook and loop material attached by sewing to the tightly woven fabric 20. As shown in FIG. 1, the bottom portions of sections 22 and 24 are covered by the pile 12. Also shown in FIG. 2 is a pair of pockets 26 and 28 respectively sewn to the top surface of the fabric 20. An opening 30 to pocket 26 and an opening 32 to pocket 28 provides a means for inserting an air bladder 34 into each pocket. Straps 40 and 42 are also sewn on to the fabric 20 with the bottom surface 36 and 38 respectively of straps 40 and 42 covered with hook and loop material. A top surface 44 and 46 respectively of straps 48 and 50 are covered by hook and loop material. The reverse side of each strap 48 and 50 has a cloth material. The top surface of projecting sections 14 and 16 are covered by fabric material. In addition to the bladder 34, either a polycentric support element 52 or a rigid support element 54, as shown respectively in FIGS. 4 and 5, are insertable into pockets 26 and 28. The preferred shape of the air bladder 34 is "hour-glass" shaped, although air bladders of other shapes could be employed with brace 10. This "hour-glass" shape is ideal to the configuration of brace 10 whereby an upper portion of the air bladder 34 lays against a lateral portion of the thigh above the knee and a lower portion of the air bladder 34 lays against a lateral portion of the calf below the knee.

FIG. 3 shows the brace 10 mounted over the knee 56 of a patient. Section 16 is folded over on to section 24 so that the hook and loop material on the bottom of section 16 engages the hook and loop material on the top of section 24. In like manner, the section 14 is passed over section 22 so that the hook and loop material on the bottom portion of section 14 engages the corresponding hook and loop material on the top portion of section 22. In the brace 10, shown in FIG. 3, a polycentric support element 52 is employed in the pocket 26 with bladder 34 so that the patient can bend his or her leg. A bulb pump 58 is attached by its valve 60 to the corresponding valve opening in bladder 34 to enable the bladder to be expanded and rigidly support the patient's knee in the designated position.

Figure 7:
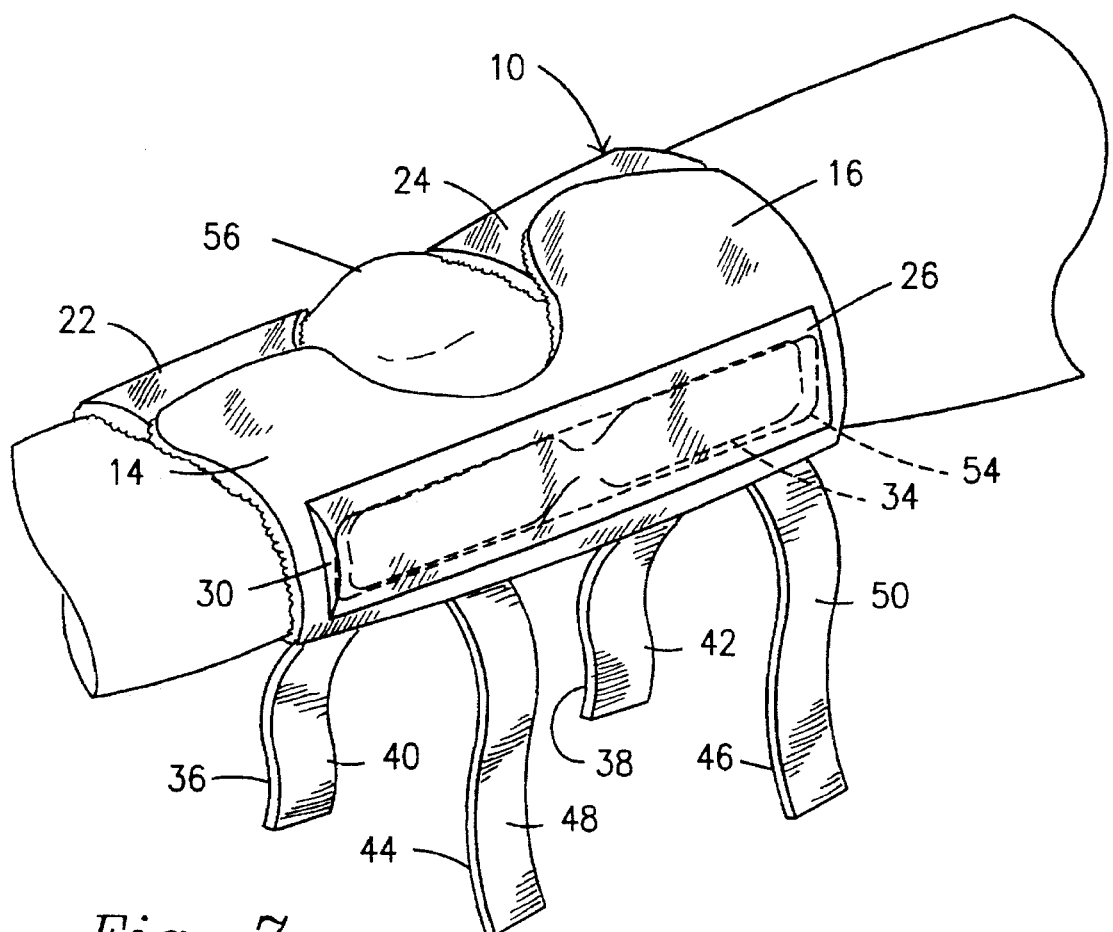
FIG. 7 is a perspective view of the orthopedic appliance shown in FIG. 1, draped over a patients knee with the air bladder and rigid support element shown in phantom.
Figure 8:
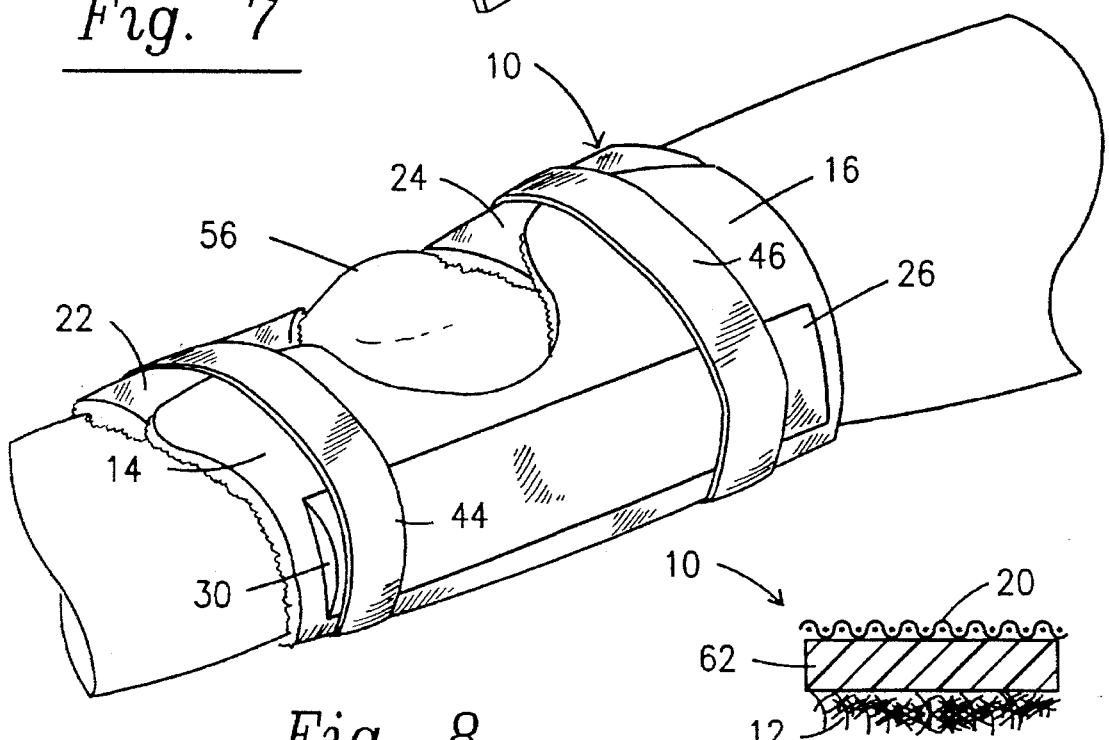
FIG. 8 is a perspective view of the orthopedic appliance shown in FIG. 1, retaining a patient's knee in a fixed position.
Figure 9:
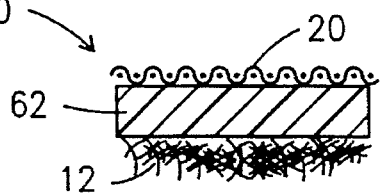
FIG. 9 is a cross sectional view through the cloth body of the orthopedic appliance shown in FIG. 1.

As shown in FIG. 7, a rigid support element 54 is employed in pocket 26 together with a bladder 34 to maintain a completely rigid configuration for the patient's leg. Top surfaces 44 and 46 of straps 48 and 50 respectively are attached to corresponding hook and loop material 36 and 38 on straps 40 and 42 respectively by wrapping around the patient's leg. This produces the configuration shown in FIG. 8, where the patient's leg is extended in a fixed position with the bladder 34 filled to maintain the leg in the fixed position. The wrapping leaves an area for the patella of the patient's knee 56 to protrude As shown in FIG. 9, the top surface of tightly woven fabric 20 is separated from the bottom portion covered by a pile 12 by an intermediate foam layer 62 so that the brace 10 has a soft wool-like material 12 in contact with the skin and a durable fabric 20 on the outside protecting the brace from environmental effects, but with a foam intermediate material to maintain the body structure of the splint while at the same time providing a soft medium to prevent pressure against the soft tissue of the leg.

The knee brace 10 of this invention is designed primarily to treat pre-fixed contracture of the knee. Such pre-fixed contracture is any contracted joint that can be flexed or extended and where splinting is indicated for treatment. The brace 10 will stabilize the extension of the knee and is useful for immobilization of the knee during post-trauma or post-surgery. In addition, the brace 10 will support post-trauma or surgery patients while undergoing rehabilitation.

In placing the brace 10 on a patient, the leg is extended as far as comfort will allow and the open brace 10 is place on the patient's knee with the section 16 placed around the thigh to contact the section 24 on the fabric, and the section 14 placed around the calf to contact the section 22 on the fabric. The pile surface 12 is placed down over the patient's skin. The air bladder is inflated to hold the leg in the degree of extension desired. The greater the degree of extension, the more inflation in the air bladder 34. If the patient is ambulating, the polycentric support element 52 is used in the pockets 26 and 28 whereas if the knee should be completely immobilized, the rigid support elements are inserted in pockets 26 and 28. After the correct air pressure is reached, the pile straps 48 and 50 are connected to straps 40 and 42 respectively. Once the amount of air pressure necessary for either stabilization or immobilization has been determined, the splint can be removed and put back on without changing the air pressure in the air bladder 34. To remove the brace 10 the straps are all unfastened. To replace the brace 10, extend the leg and place the brace 10 pile side 12 toward and under the leg and fasten the wide straps over and under the knee. One finger should be inserted under all edges for correct clearance. The brace 10 can be easily removed and replaced in order to treat wounds under the splinted area.

Referring to FIGS. 10, 11, 14 and 15, a preferred embodiment of the knee brace 64 is provided. As shown in FIG. 10, the preferred brace 64 has the pair of longitudinal pockets 26 and 28 attached to the tightly woven fabric 20 surrounding the hole 18 located generally in the center of brace 64. The pair of openings 30 and 32 in pockets 26 and 28 respectively, permit the air bladder 34 as well as polycentric support element 52 (see FIG. 4) and rigid support element (see FIG. 5) to be inserted within pockets 26 and 28. The air bladder 34, inflatable by bulb pump 58, provides a means to slowly expand a contracted muscle. Once the desired position of the knee has been obtained, either a polycentric or rigid support element, 52 and 54 respectively, is inserted within longitudinal pockets 26 and 28, thereby retaining the knee in a fixed position.

Referring to FIGS. 10, 11, 14, and 15, a pair of latitudinal pockets 66 and 68 are sewn to the tightly woven fabric 20 of preferred brace 64. Latitudinal pockets 66 and 68 have openings 70 and 72 respectively for receiving a flexible support element 74. FIGS. 12 and 13 respectively show flexible support element 74 before and after its shape has been manipulated. The position of latitudinal pockets 66 and 68 permit flexible support element 74 to surround the posterior portion of a patient's thigh and calf, above and below the posterior section of the patient's knee respectively. Flexible support element 74 provides medial support to the tendons along the posterior portion of the thigh and calf.

Figure 14:
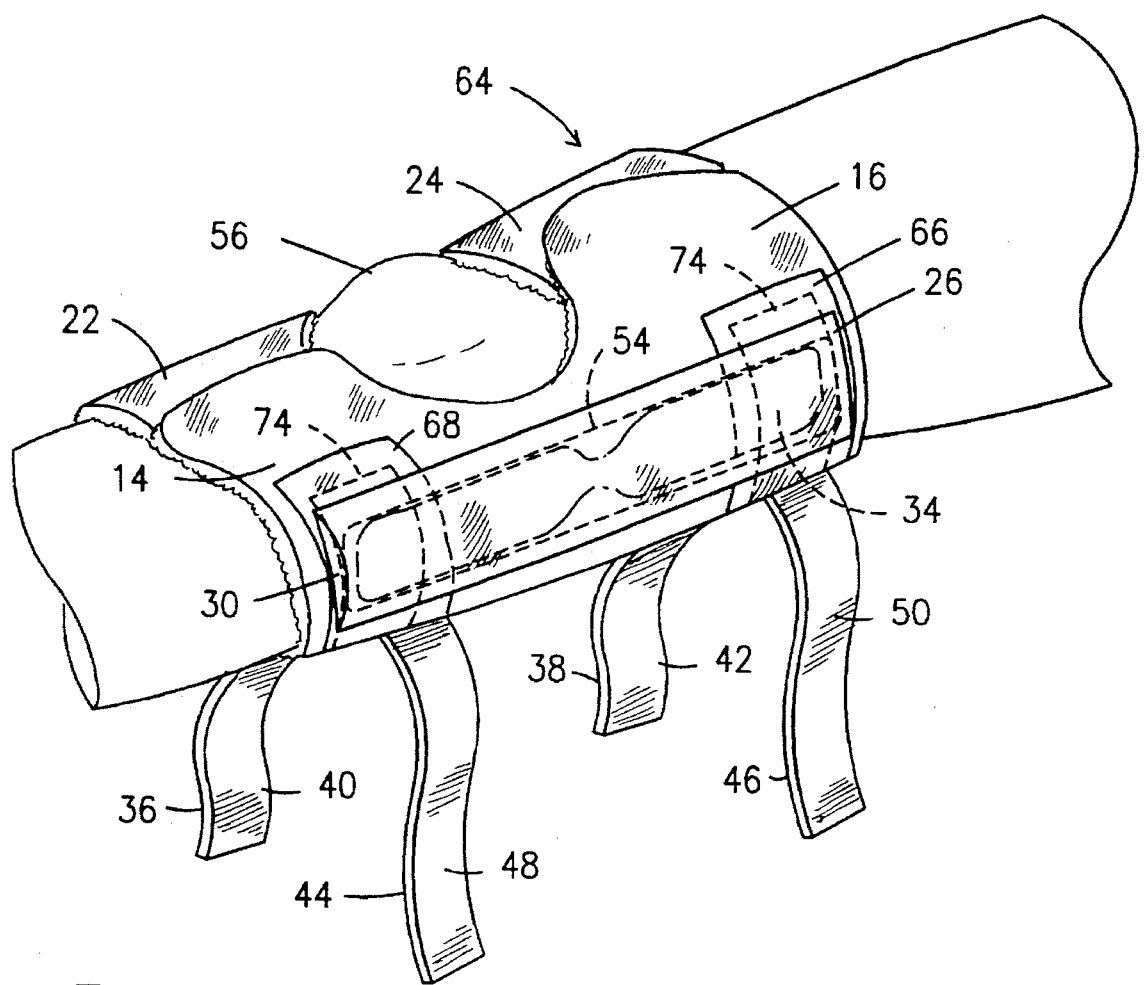
FIG. 14 is a perspective view of the preferred orthopedic appliance draped over a patient's knee with the air bladder and rigid support element shown in phantom.
Figure 15:
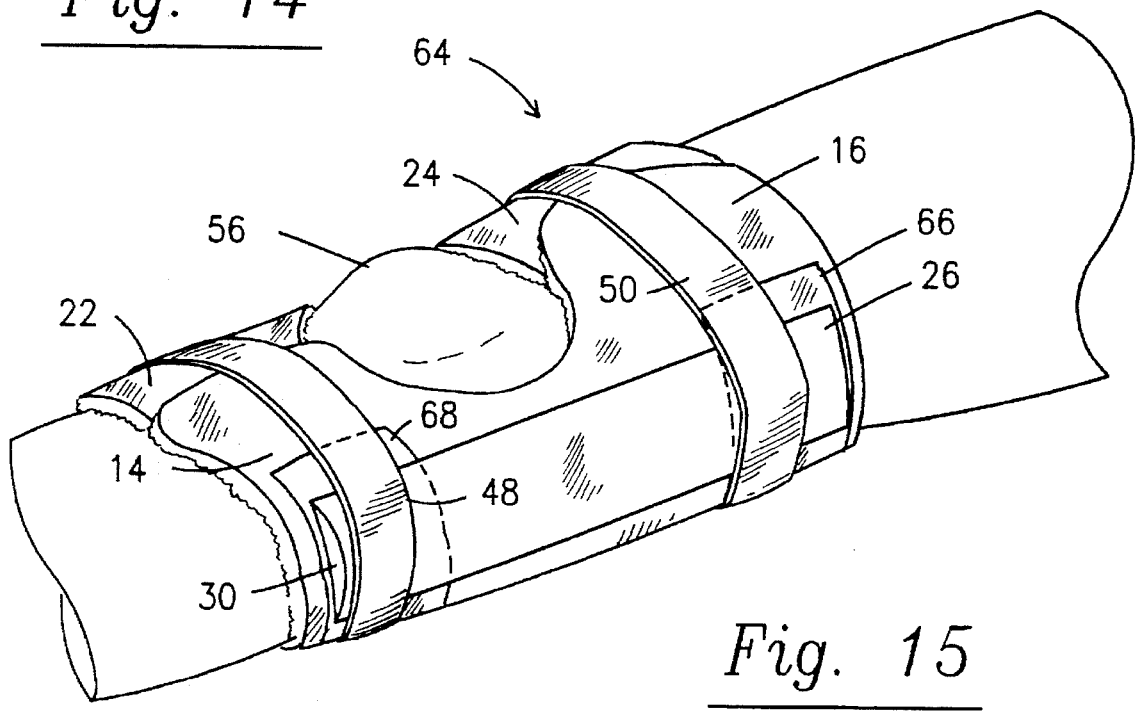
FIG. 15 is a perspective view of the preferred orthopedic appliance retaining a patient's knee in a fixed position.

Referring to FIGS. 10, 11, 14, and 15, preferred brace 64 has the pair of projecting sections 14 and 16 respectively engaging the pair of projecting sections 22 and 24 providing a means for wrapping the brace 64 around a knee of a patient. Bottom portions of sections 14 and 16 contain hook and loop material for respectively engaging corresponding hook and loop material on top portions of sections 22 and 24. As shown in FIGS. 11, 14, and 15, the employed brace 64 provides an open area from which a patella portion of a knee 56 can protrude. Brace 64 is wrapped around a knee 56 of a patient such that hole 18 exposes a posterior portion of knee 56. A bottom portion (not shown) of brace 64 is covered by pile 12 of the same type as shown and described in the embodiment of FIG. 1. Brace 64 is secured to a patient's knee by hook and loop material 44 and 46 of straps 48 and 50 respectively engaging hook and loop material 36 and 38 of straps 40 and 42, as shown in FIG. 14. Referring to FIG. 15, brace 64 is deployed to a patient's knee and set in a desired fixed position, with all respective hook and loop material engaging one another.

Figure 16:
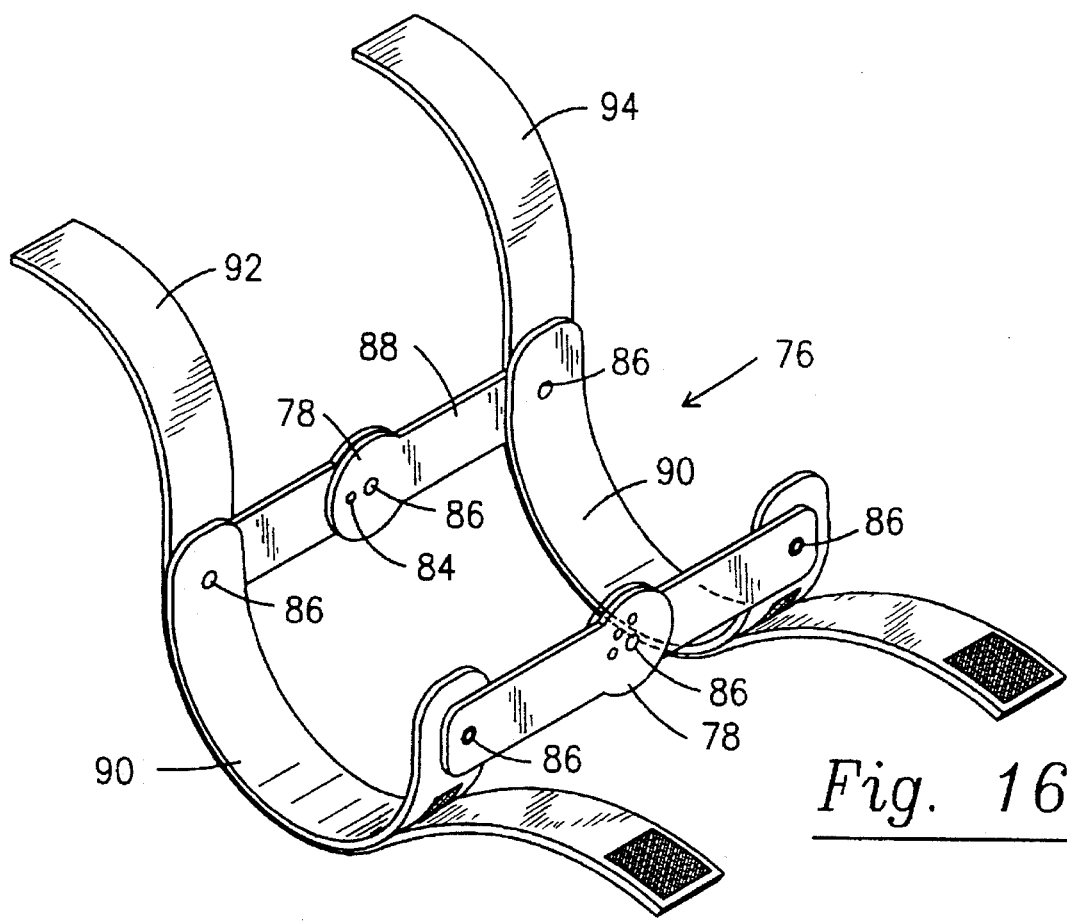
FIG. 16 is a perspective view of an exoskeleton frame having hinged support portion for use with the orthopedic appliance of my invention.
Figure 18:
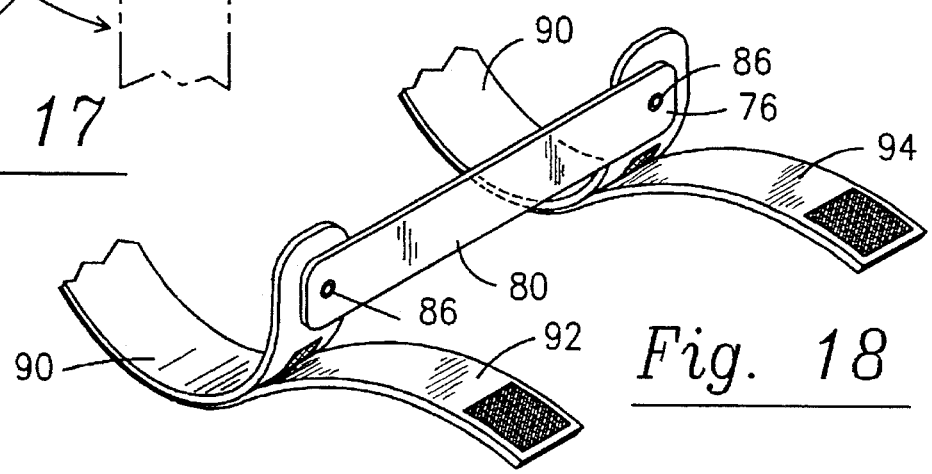
FIG. 18 is a partial perspective view of an exoskeleton frame having a rigid support portion for use with the orthopedic appliance of my invention.
Figure 19:
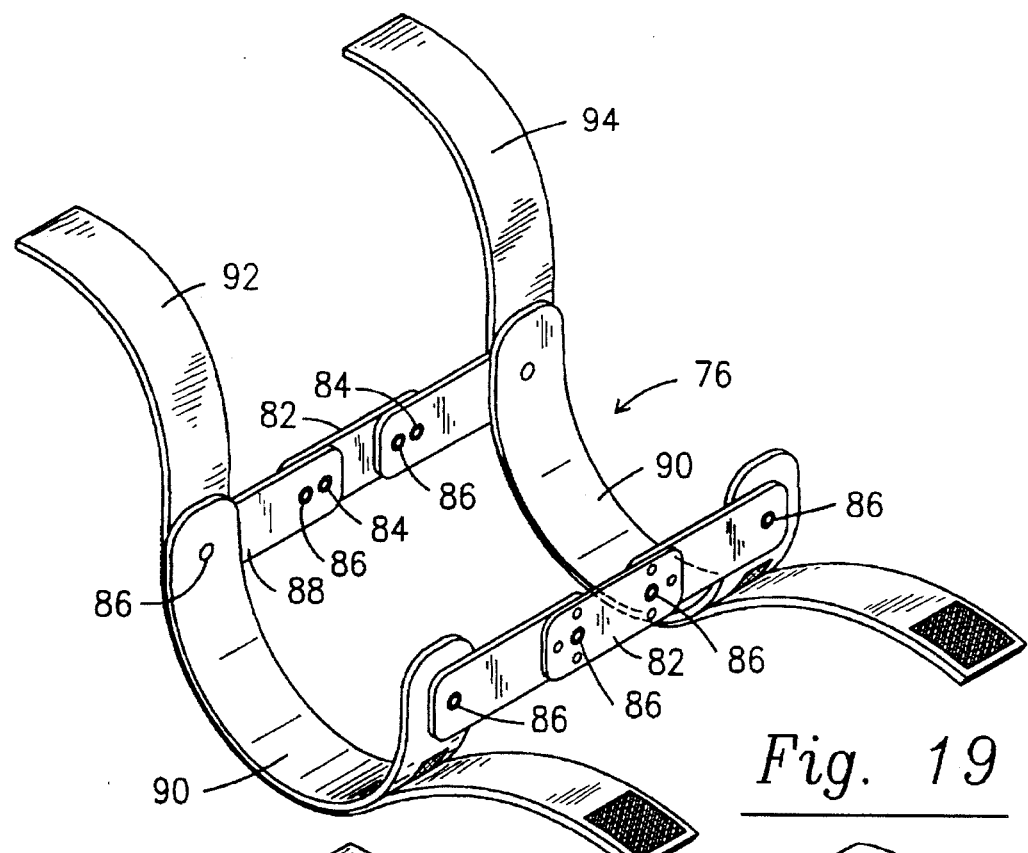
FIG. 19 is a perspective view of an exoskeleton frame having a polycentric support portion for use with the orthopedic appliance of my invention.
Figure 20:
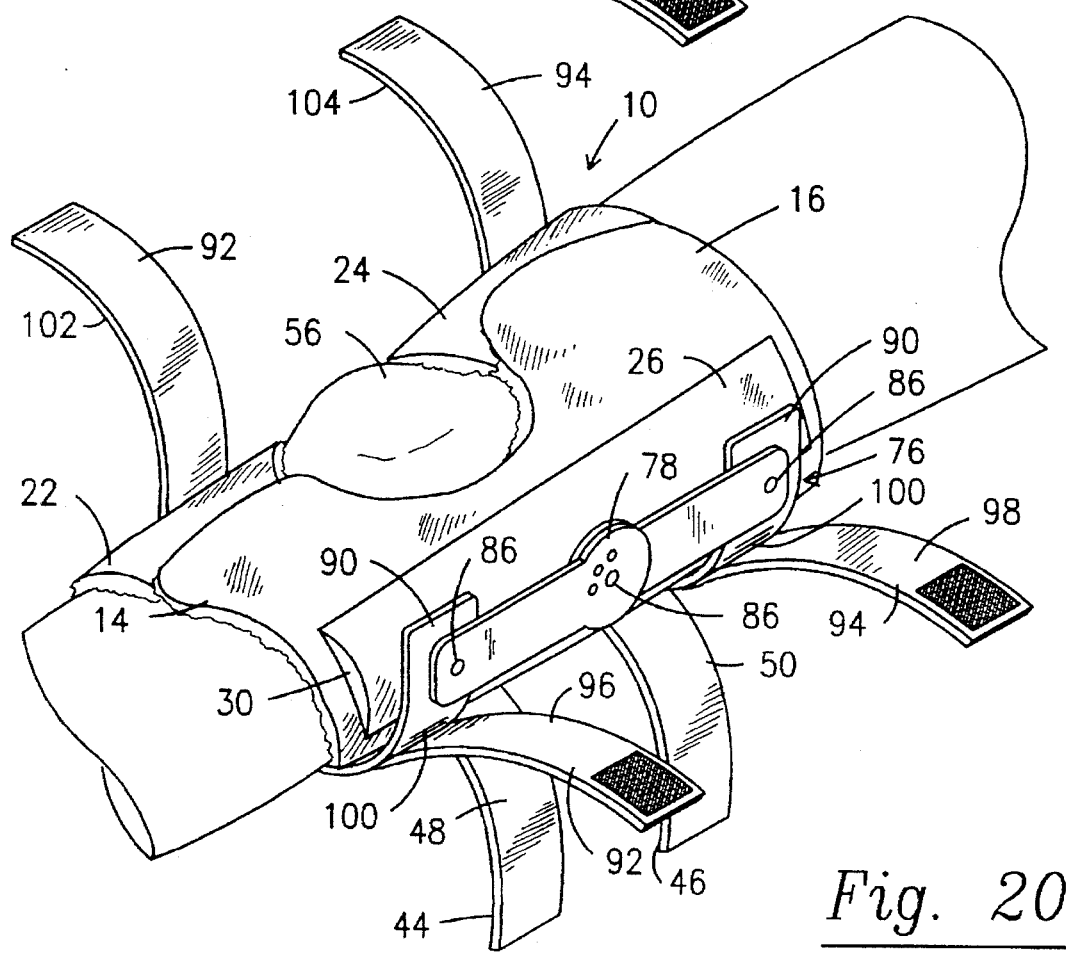
FIG. 20 is a perspective view of the orthopedic appliance of FIG. 2 with the exoskeleton frame draped over a patient's knee, the exoskeleton frame having a hinged support portion.
Figure 21:
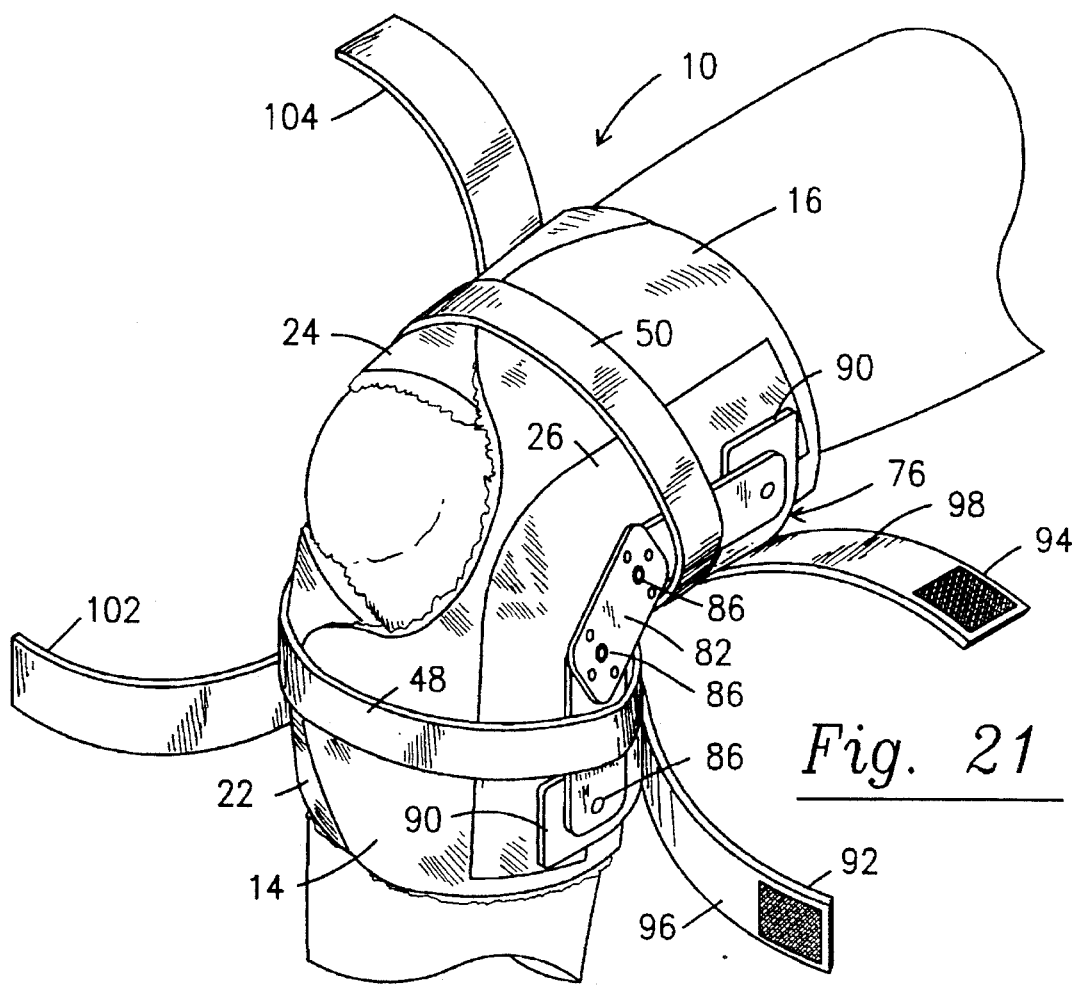
FIG. 21 is a perspective view of the orthopedic appliance of FIG. 2 with the exoskeleton frame retaining a patient's knee in a fixed position, the exoskeleton frame having a polycentric support portion.

Referring to FIGS. 16, 18, and 19, an exoskeleton frame 76 is provided for use with either brace 10 or brace 64. Exoskeleton frame 76 is positioned around brace 10 or brace 64 and replaces polycentric or rigid support elements, 52 and 54 respectively, and flexible support element 74 in brace 64. FIGS. 20 and 21 show exoskeleton frame 76 employed around brace 10. If exoskeleton frame 76 is used with brace 64, latitudinal pockets 66 and 68 are not used.

Figure 17:
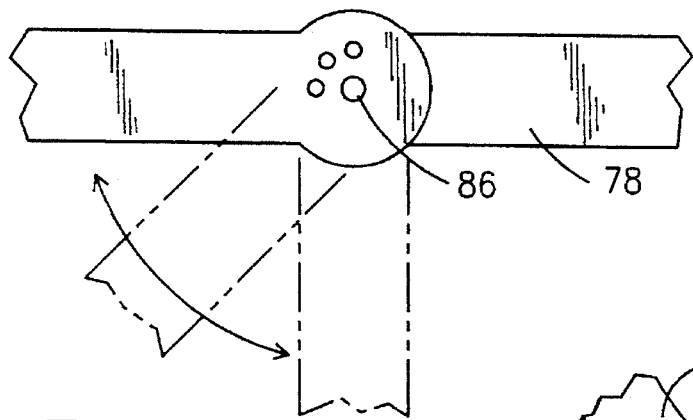
FIG. 17 is a side view in partial phantom of a portion the exoskeleton frame illustrating the different positions in which the hinged support portion can be set.

Exoskeleton frame 76 is provided with a plurality of interchangeable support portions for setting a knee of a patient in a variety of fixed positions. FIG. 16 shows exoskeleton frame 76 having a preferred hinged support portion 78. FIG. 17 illustrates the variety of fixed positions in which hinged support portion 78 of exoskeleton frame 76 can be set. FIG. 18 shows exoskeleton frame 76 having a rigid support portion 80. FIG. 19 shows exoskeleton frame 76 having a polycentric support portion 82. Polycentric support portion 82 allows exoskeleton frame 76 to be locked in a variety of fixed positions as shown in FIGS. 19 and 21. Hinged support portion 78 and polycentric support portion 82 are locked in their respective fixed position by a preferred push button mechanism 84, although removable screws (not shown) could be employed to achieve the same result. The push button mechanism 84 is engagable from an inner surface 88 along hinged support portion 78 and polycentric support portion 82, as shown in FIGS. 16 and 19 respectively. A plurality of Chicago screws 86 permit rotation of hinged support portion 78 and polycentric support portion 82. As shown in FIGS. 16, 18, and 19, a pair of flexible support portions 90 are provided with exoskeleton frame 76 to provide medial support to the tendons along the posterior portion of the thigh and calf. Flexible support portions 90 are rotatably attached to either hinged, rigid, or polycentric support portions 78, 80, and 82 respectively, by Chicago screws 86.

Referring to FIGS. 20 and 21, exoskeleton frame 76 is employed with brace 10 such that straps 40, 42, 48 and 50 of brace 10 surround exoskeleton frame 76. A pair of straps 92 and 94 attach to exoskeleton frame 76 and then surround straps 40, 42, 48, and 50 of brace 10, thereby securing exoskeleton frame 76 to brace 10. Bottom surfaces 96 and 98 of straps 92 and 94 respectively are attached to exoskeleton frame 76 along an outer surface 100 of flexible support portions 90 by hook and loop material, as shown in FIG. 20. Hook and loop material along bottom surfaces 96 and 98 of straps 92 and 94 respectively at a tip portion, engages a top surface 102 and 104 of straps 92 and 94 respectively, at an opposed tip portion. Exoskeleton frame 76 is used with and secured to brace 64 in the identical manner as with brace 10.

Figure 22:
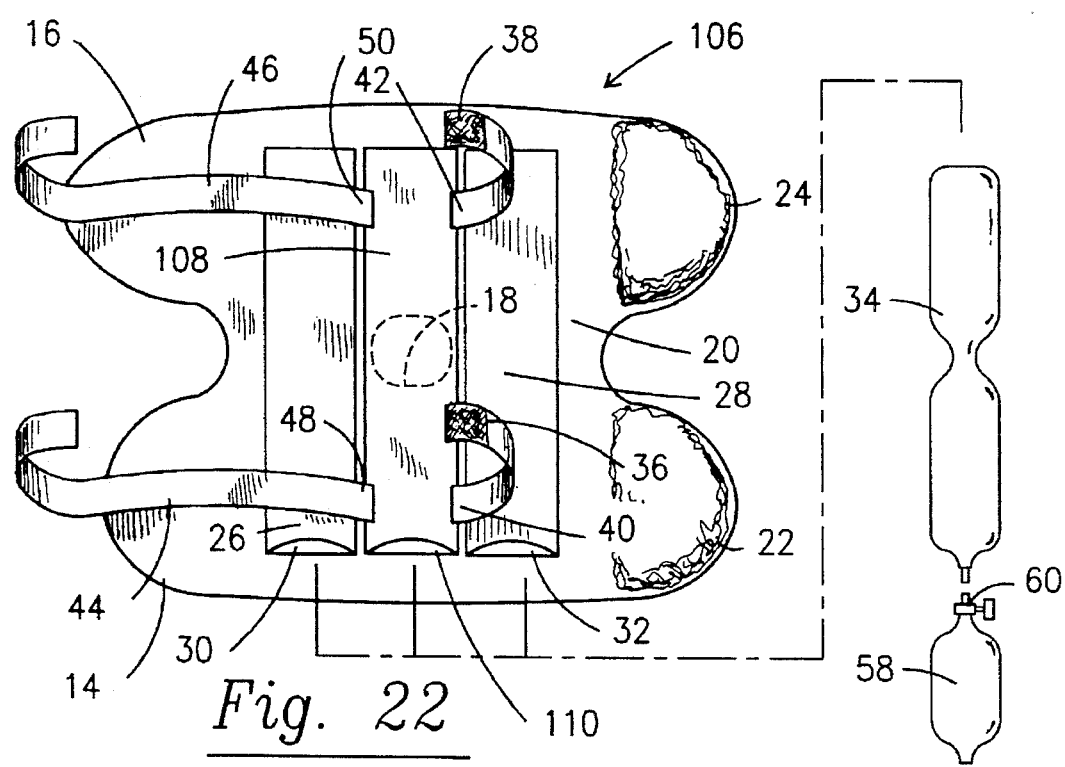
FIG. 22 is a top plan view of an alternate embodiment of the orthopedic appliance of my invention.

Referring to FIG. 22, an alternate knee brace 106 is provided. Brace 106 has the pair of longitudinal pockets 26 and 28 sewn to the tightly woven fabric 20 surrounding the hole 18 located generally in the center of brace 106. The pair of openings 30 and 32 in pockets 26 and 28 respectively permit the air bladder 34 as well as polycentric support element 52 (see FIG. 4) and rigid support element (see FIG. 5) to be inserted within pockets 26 and 28. The air bladder 34, inflatable by bulb pump 58, provides a means to slowly expand a contracted muscle. Once the desired position of the knee has been obtained, either a polycentric or rigid support element, 52 or 54 respectively, is inserted within longitudinal pockets 26 and 28, thereby setting the knee in a fixed position.

Referring to FIG. 22, brace 106 has an additional longitudinal center pocket 108 sewn to the tightly woven fabric, located intermediate longitudinal pockets 26 and 28, covering hole 18 from the top side of brace 106. Center pocket 108 has an opening 110 for receiving air bladder 34 for providing dynamic pressure directly to a knee contracture. The configuration of brace 106 provides medial and lateral air pressure for stretching the knee tendons, while the dynamic pressure of air bladder 34 within center pocket 108 offers a complimentary "pushing" action against the tendons, facilitating the expansion of the knee contracture.

Figure 23:
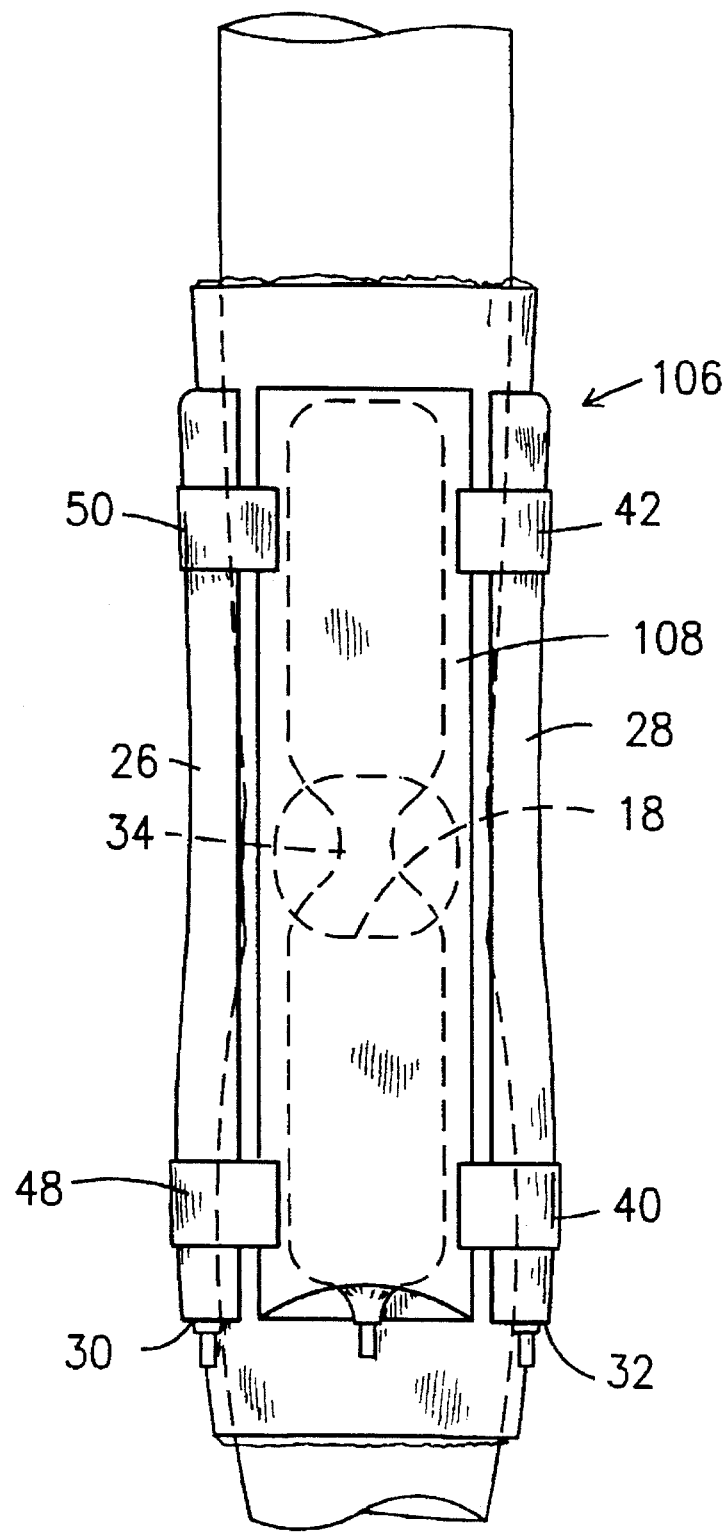
FIG. 23 is a posterior view of a patient's knee with the alternate embodiment of FIG. 22 retaining the knee in a fixed position.

Referring to FIG. 22, brace 106 has the pair of projecting sections 14 and 16 respectively engaging the pair of projecting sections 22 and 24 providing a means for wrapping the brace 106 around a knee of a patient. Bottom portions of sections 14 and 16 contain hook and loop material for respectively engaging corresponding hook and loop material on top portions of sections 22 and 24. Brace 106 provides an open area from which a patella portion of a knee 56 can protrude when employed on a patient's knee. Brace 106 is wrapped around a knee 56 of a patient such that hole 18 exposes a posterior portion of knee 56, as shown in phantom in FIG. 23. A bottom portion (not shown) of brace 106 is covered by pile 12 of the same type as shown and described in the embodiment of FIG. 1. and FIG. 10. Brace 106 is secured to a patient's knee by hook and loop material 44 and 46 of straps 48 and 50 respectively engaging hook and loop material 36 and 38 of straps 40 and 42, as shown in FIG. 22. Brace 106 can be used with exoskeleton frame 76 or without. Exoskeleton frame 76 is used with and secured to brace 106 in the identical manner as with brace 10.

Equivalent materials can be substituted for the materials employed in this invention to obtain substantially the same result in the same way.

Having thus described the invention what is claimed and desired to be secured by Letters Patent is:

1. An orthopedic appliance for surrounding a knee of a patient to treat knee flexion contractures, the appliance comprising, a cloth body having a top and bottom layer, a foam layer located intermediate the top and bottom layers, and a generally centrally located hole, the top layer covered by a tightly woven fabric, the bottom layer covered by a soft non-abrasive material for contact with the skin of the patient, the cloth body wrapped around the knee of the patient such that an area is provided from which a patella portion of the knee can protrude and the centrally located hole exposes a posterior portion of the knee, hook and loop straps attached to the top layer of the cloth body for securing the cloth body in a wrapped position, at least two longitudinal pockets integrally attached to the top layer of the cloth body, each longitudinal pocket having an opening formed therein, an air bladder mounted within each longitudinal pocket, the air bladders permitting inflation to rigidly set the knee in a desired position and deflation so that the patient can flex the knee, the air bladders having been inserted through the openings in the longitudinal pockets, and a longitudinal support element mounted within each longitudinal pocket adjacent the air bladder for providing lateral and medial support to the orthopedic appliance, the longitudinal support elements having been inserted through the openings formed in the pockets.

2. The orthopedic appliance for surrounding a knee of a patient to treat knee flexion contractures according to claim 1, the appliance having in addition, at least two latitudinal pockets integrally attached to the top layer of the cloth body, each latitudinal pocket having an opening formed therein, and a flexible support element mounted within each latitudinal pocket for providing medial support to tendons of the knee flexion contracture above and below the posterior portion of the knee, the flexible support elements having been inserted through the openings in the latitudinal pockets.

3. The orthopedic appliance for surrounding a knee of a patient to treat knee flexion contractures according to claim 1, wherein an air bladder is mounted within each of two longitudinal pockets, the longitudinal pockets located on opposite sides of the generally centrally located hole.

4. The orthopedic appliance for surrounding a knee of a patient to treat knee flexion contractures according to claim 1, wherein three longitudinal pockets are provided, two longitudinal pockets located on opposite sides of the generally centrally located hole, and a third longitudinal pocket covering the generally centrally located hole, the third longitudinal pocket containing an air bladder to provide dynamic pressure to tendons of the knee flexion contracture above and below a middle posterior portion of the knee.

5. The orthopedic appliance for surrounding a knee of a patient to treat knee flexion contractures according to claim 1, wherein the longitudinal support elements are polycentric to permit the patient's knee to be set in a variety of fixed positions.

6. The orthopedic appliance for surrounding a knee of a patient to treat knee flexion contractures according to claim 1, wherein the longitudinal support elements are rigid to restrict movement of the knee, the longitudinal support elements setting the knee in a straight and fixed position.

7. The orthopedic appliance for surrounding a knee of a patient to treat knee flexion contractures according to claim 2, wherein two latitudinal pockets are provided above and below the generally centrally located hole, each latitudinal pocket containing one flexible support element, the flexible support element adapted to be contoured to the shape of the posterior portion of a thigh and calf of the patient.

8. An orthopedic appliance for surrounding a knee of a patient to treat knee flexion contractures, the appliance comprising, a cloth body having a top and bottom layer, a foam layer located intermediate the top and bottom layers, and a generally centrally located hole, the top layer covered by a tightly woven fabric the bottom layer covered by a soft non-abrasive material for contact with the skin of the patient, the cloth body wrapped around the knee of the patient such that an area is provided from which a patella portion of the knee can protrude and the centrally located hole exposes a posterior portion of the knee, hook and loop straps attached to the top layer of the cloth body for securing the cloth body in a wrapped position, at least two longitudinal pockets integrally attached to the top layer of the cloth body, each longitudinal pocket having an opening formed therein, an air bladder mounted within each longitudinal pocket, the air bladders permitting inflation to rigidly set the knee in a desired position and deflation so that the patient can flex the knee, the air bladders having been inserted through the openings in the longitudinal pockets, and an exoskeleton frame surrounding the cloth body and having a pair of stiff support portions rotatably attached to a pair of flexible support portions at opposed ends of the stiff and flexible support portions respectively, the pair of the flexible support portions for surrounding a posterior portion of a thigh and calf of the patient, the stiff support portions for positioning along opposed sides of the knee adjacent the air bladders, the flexible support portions having an outer surface for attaching a pair of hook and loop straps by hook and loop material, and the hook and loop straps securing the exoskeleton frame around the cloth body of the orthopedic appliance.

9. The orthopedic appliance for surrounding a knee of a patient to treat knee flexion contractures according to claim 8, wherein the pair of stiff support portions are hinged to permit the patient's knee to be set in a variety of fixed positions.

10. The orthopedic appliance for surrounding a knee of a patient to treat knee flexion contractures according to claim 8, wherein the pair of stiff support portions are rigid to restrict movement of the knee, the support portions setting the knee in a straight and fixed position.

11. The orthopedic appliance for surrounding a knee of a patient to treat knee flexion contractures according to claim 8, wherein the pair of stiff support portions are polycentric to permit movement of the knee and to allow the knee to be set in a variety of fixed positions.

12. An orthopedic appliance for surrounding a knee of a patient to treat knee flexion contractures, the appliance comprising, a cloth body having a top and bottom layer, a foam layer located intermediate the top and bottom layers, and a generally centrally located hole, the top layer covered by a tightly woven fabric, the bottom layer covered by a soft non-abrasive material for contact with the skin of the patient, the cloth body-wrapped around the knee of the patient such that an area is provided from which a patella portion of the knee can protrude and the centrally located hole exposes a posterior portion of the knee, hook and loop straps attached to the top layer of the cloth body for securing the cloth body in a wrapped position two longitudinal pockets integrally attached to the top layer of the cloth body on opposed sides of the generally centrally located hole, each longitudinal pocket having an opening formed therein, an air bladder mounted within each of the two longitudinal pockets, the air bladders permitting inflation to rigidly set the knee in a desired position and deflation so that the patient can flex the knee, the air bladders having been inserted through the openings in the longitudinal pockets, a longitudinal support element mounted within each of the two longitudinal pockets for providing lateral support to the orthopedic appliance, the longitudinal support elements having been inserted through the openings formed in the pockets, the support elements mounted adjacent the air bladders, two latitudinal pockets integrally attached to the top layer of the cloth body above and below the generally centrally located hole, each latitudinal pocket having a opening formed therein, and a flexible support element mounted within each of the two latitudinal pockets for providing medial support to tendons of the knee flexion contracture above and below the posterior portion of the knee, the flexible support elements having been inserted through the openings in the latitudinal pockets.

13. The orthopedic appliance for surrounding a knee of a patient to treat knee flexion contractures according to claim 12, wherein the longitudinal support elements are polycentric to permit the patient's knee to be set in a variety of fixed positions.

14. The orthopedic appliance for surrounding a knee of a patient to treat knee flexion contractures according to claim 12, wherein the longitudinal support elements are rigid to restrict movement of the knee, the longitudinal support elements setting the knee in a straight and fixed position.

15. The orthopedic appliance for surrounding a knee of a patient to treat knee flexion contractures according to claim 12, wherein the air bladders are hour-glass shaped.

16. The orthopedic appliance for surrounding a knee of a patient to treat knee flexion contractures according to claim 12, wherein the soft non-abrasive material on the bottom layer of the cloth body is a synthetic wool pile.

17. The orthopedic appliance for surrounding a knee of a patient to treat knee flexion contractures according to claim 12, wherein the air bladder contains a valve to permit ingress and egress of air.

* * * * *